(12) United States Patent
Alqam et al.

(10) Patent No.: US 9,557,254 B2
(45) Date of Patent: Jan. 31, 2017

(54) PORTABLE DEVICE AND METHOD FOR FIELD TESTING PROPPANT

(71) Applicant: Saudi Arabian Oil Company, Dhahran (SA)

(72) Inventors: Mohammad H. Alqam, Dhahran (SA); Hazim Husain Abass, Dhahran (SA); Hussain A. Al-Shammary, Dammam (SA); Edwin T. Caliboso, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 448 days.

(21) Appl. No.: 13/788,874

(22) Filed: Mar. 7, 2013

(65) Prior Publication Data

US 2013/0233536 A1  Sep. 12, 2013

Related U.S. Application Data

(60) Provisional application No. 61/607,633, filed on Mar. 7, 2012.

(51) Int. Cl.
*G01N 3/00* (2006.01)
*E21B 43/267* (2006.01)
(Continued)

(52) U.S. Cl.
CPC ............ *G01N 3/00* (2013.01); *C09K 8/805* (2013.01); *E21B 43/267* (2013.01); *G01N 3/08* (2013.01);
(Continued)

(58) Field of Classification Search
CPC .... G01N 3/00; G01N 15/0806; G01N 33/442; G01N 3/08; E21B 43/267; C09K 8/805
(Continued)

(56) References Cited

U.S. PATENT DOCUMENTS 2,810,289 A   10/1957  Button
3,635,078 A    1/1972  Wissa
(Continued)

FOREIGN PATENT DOCUMENTS

WO   2010058045 A2   5/2010
WO   2010130037 A1   11/2010

OTHER PUBLICATIONS

New England Research, Inc., Laboratory Systems and AutoLab Series webpages Oct. 3, 2011 and Oct. 10, 2009.*
(Continued)

*Primary Examiner* — Michael A Lyons
*Assistant Examiner* — David L Singer
(74) *Attorney, Agent, or Firm* — Bracewell LLP; Constance G. Rhebergen; Keith R. Derrington

(57) ABSTRACT

A testing system and method for evaluating the time required for shutting in a well after packing fractures in the well with a proppant having curable resin. At the well site, a sample of the proppant is compressed and heated in a portable unit. While the sample is being heated and compressed, its properties are being monitored to determine if the resin in the proppant has cured. Recording the time required for the proppant to cure provides an indication of how long to shut in the well after packing the fractures with the proppant. The portable unit includes a gas to fluid intensifier for compressively stressing the sample and a heat source for heating the sample. Sensors adjacent the proppant sample monitor the properties.

15 Claims, 3 Drawing Sheets

(51) Int. Cl.
*G01N 3/08* (2006.01)
*G01N 15/08* (2006.01)
*G01N 33/44* (2006.01)
*C09K 8/80* (2006.01)

(52) U.S. Cl.
CPC ........ *G01N 15/0806* (2013.01); *G01N 33/442* (2013.01)

(58) Field of Classification Search
USPC .................. 166/250.01; 73/152.39, 825, 826
See application file for complete search history.

(56) References Cited

U.S. PATENT DOCUMENTS

| | | | |
|---|---|---|---|
| 3,929,191 A | | 12/1975 | Graham et al. |
| 4,749,038 A | | 6/1988 | Shelley |
| 4,791,822 A | | 12/1988 | Penny |
| 4,918,993 A | | 4/1990 | Hughson |
| 5,018,396 A | | 5/1991 | Penny |
| 5,062,303 A | * | 11/1991 | Gould ...................... G01N 3/12 73/798 |
| 5,746,293 A | * | 5/1998 | Engle ........................ 188/151 R |
| 5,791,415 A | | 8/1998 | Nguyen et al. |
| 5,844,136 A | | 12/1998 | Marsala et al. |
| 5,960,880 A | | 10/1999 | Nguyen et al. |
| 6,059,034 A | | 5/2000 | Rickards et al. |
| 6,114,410 A | | 9/2000 | Betzold |
| 6,675,112 B1 | | 1/2004 | Chadwick |
| 6,729,404 B2 | | 5/2004 | Nguyen et al. |
| 6,745,159 B1 | | 6/2004 | Todd et al. |
| 6,887,834 B2 | | 5/2005 | Nguyen et al. |
| 6,962,200 B2 | | 11/2005 | Nguyen et al. |
| 7,032,667 B2 | | 4/2006 | Nguyen et al. |
| 7,252,146 B2 | | 8/2007 | Slabaugh et al. |
| 7,387,161 B2 | | 6/2008 | Abass et al. |
| 7,712,525 B2 | | 5/2010 | Abass et al. |
| 7,712,526 B2 | | 5/2010 | Morgan et al. |
| 7,963,330 B2 | | 6/2011 | Nguyen et al. |
| 2007/0137859 A1 | | 6/2007 | Abass et al. |
| 2008/0060444 A1 | | 3/2008 | Conway et al. |
| 2008/0135246 A1 | | 6/2008 | Canova et al. |
| 2009/0306898 A1 | | 12/2009 | Anschutz et al. |
| 2010/0282462 A1 | * | 11/2010 | Xu .......................... C09K 8/805 166/271 |
| 2011/0094295 A1 | | 4/2011 | Meadows et al. |
| 2011/0232368 A1 | | 9/2011 | Al-Dhafeeri et al. |

OTHER PUBLICATIONS

Georgia State University, HyperPhysics: Pascal's Principle, 2000.*
Trinkel, Hydraulics & Pneumatics, Oct. 16, 2006, Chapter 5: Pneumatic and hydraulic systems.*
ASTM International, D2166—06 StandardTest Method for Unconfined Compressive Strength of Cohesive Soil, 2007.*
PCT Int'l Search Report and Written Opinion dated Jul. 9, 2013; Int'l Application No. PCT/US2013/029673; Int'l Filing Date: Mar. 7, 2013.

* cited by examiner

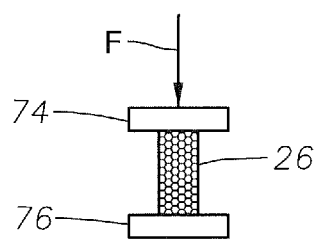
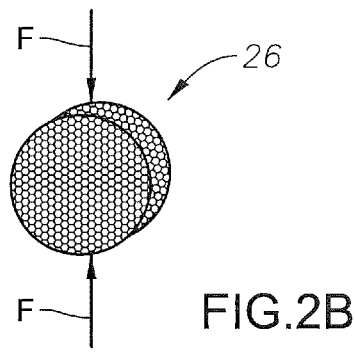
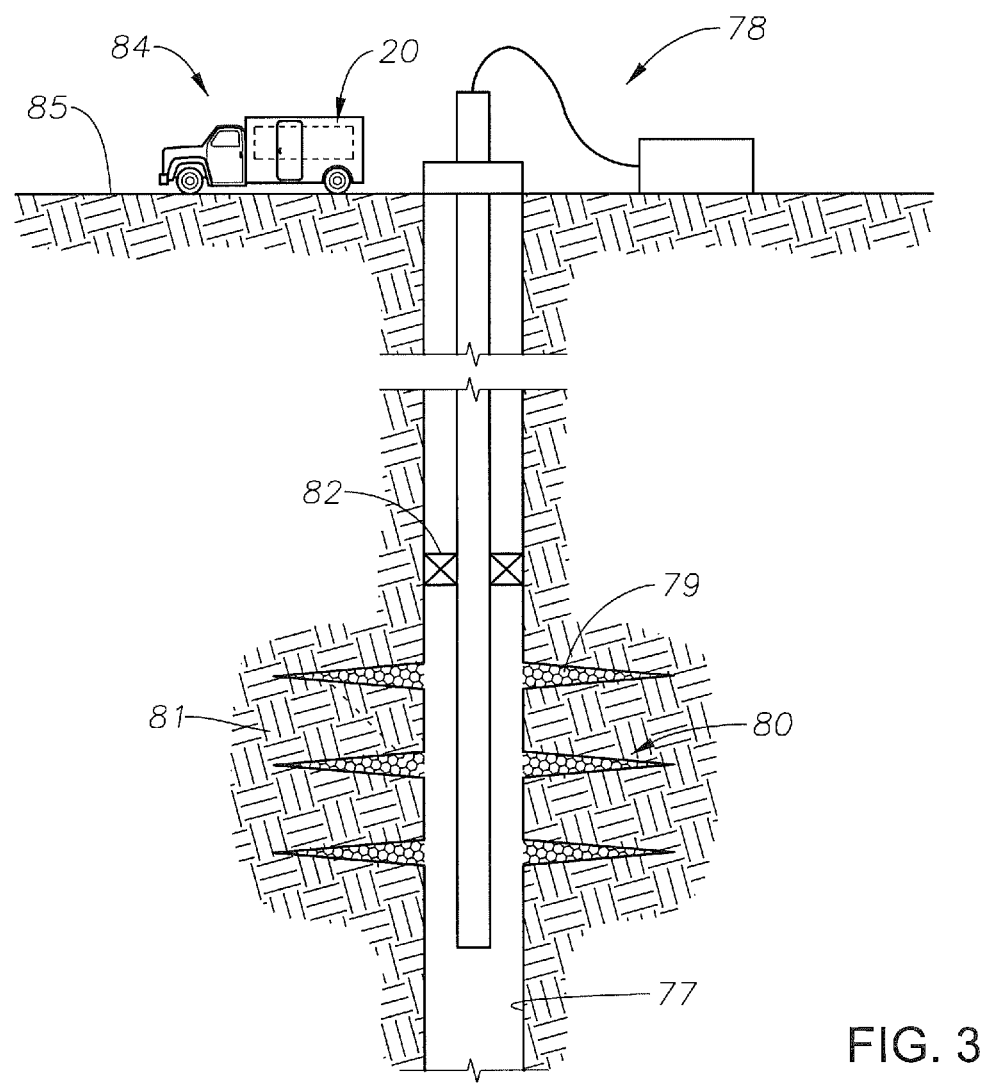
FIG. 3

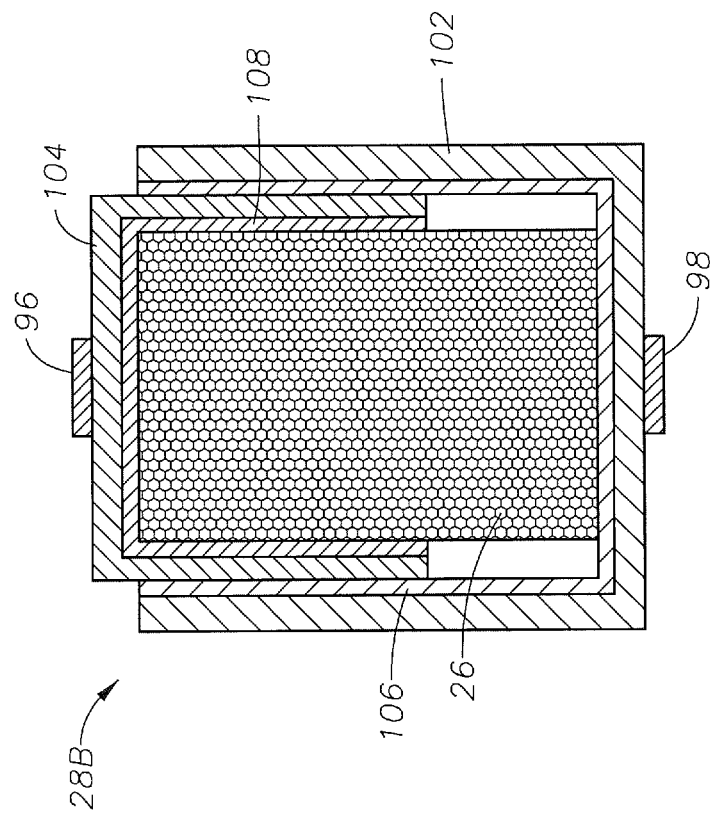
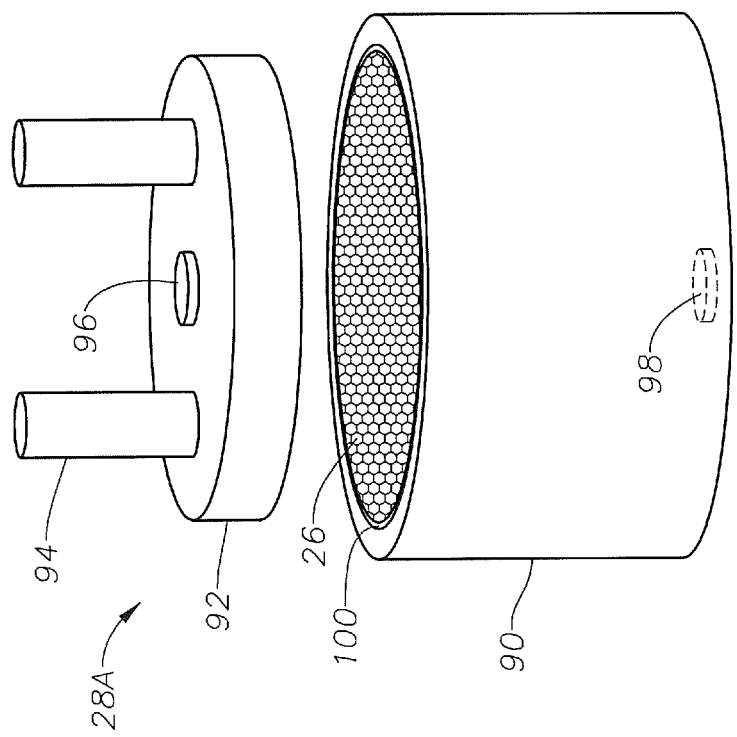
FIG. 4
FIG. 5

PORTABLE DEVICE AND METHOD FOR FIELD TESTING PROPPANT

CROSS REFERENCE TO RELATED APPLICATIONS

This application claims priority to and the benefit of U.S. Provisional Application Ser. No. 61/607,633, filed Mar. 7, 2012, the full disclosure of which is hereby incorporated by reference herein for all purposes.

BACKGROUND OF THE INVENTION

1. Field of the Invention

The present invention relates to a system and method for completing a wellbore. More specifically, the invention relates to a device that is portable to a wellbore and used for field testing of proppant.

2. Description of the Related Art

Hydrocarbon producing wellbores extend subsurface and intersect subterranean formations where hydrocarbons are trapped. The wellbores generally are created by drilling system having a drill bit mounted on an end of a drill string made up of tubulars threaded together. Usually a drive system is used to rotate the drill string and bit, and is set above an opening to the wellbore. As the bit is rotated, cutting elements on the drill bit scrape the bottom of the wellbore and excavate material thereby deepening the wellbore. Drilling fluid is typically pumped down the drill string and directed from the drill bit into the wellbore. The drilling fluid flows back up the wellbore in an annulus between the drill string and walls of the wellbore. Cuttings produced while excavating are carried up the wellbore with the circulating drilling fluid.

Sometimes fractures are created in the wall of the wellbore that extend into the formation adjacent the wellbore. Fracturing is typically performed by injecting high pressure fluid into the wellbore and sealing off a portion of the wellbore. Fracturing generally initiates when the pressure in the wellbore exceeds the rock strength in the formation. Packing the fractures with a proppant, such as sand or resin coated particles, supports the fractures and blocks sand production or other particulate matter from the formation into the wellbore.

When the fractures are packed with resin coated proppant, the well is typically shut in for a period of time to cure the resin before fluid is produced from the well. Producing from a well whose fractures have uncured resin coated proppant introduces a risk of proppant flowing out of the fractures along with the produced fluid. The time to cure the resin may vary depending on pressure and temperature in the well. Known methods of estimating a shut in time include, curing samples of proppant at an estimated wellbore pressure and temperature, and monitoring the sample over time to determine when the resin cures.

SUMMARY OF THE INVENTION

Disclosed herein are methods and devices for analyzing a proppant used in a wellbore. In an example a method of analyzing a proppant includes providing a proppant sample testing device and transporting the testing device to a wellsite having a wellbore in which proppant is being disposed. A sample of the proppant is put into the testing device, where the sample of proppant is subjected to an estimated wellbore environment. While in the device, properties of the sample of proppant are monitored over time, and a cure time of the proppant is determined based on the step of monitoring the properties of the proppant. The method can further include shutting in the wellbore after proppant is disposed in the wellbore for a period of time to define a shut in time. In this example, the shut in time is substantially the same as the determined cure time. This example can further include producing from the well after the expiration of the shut in time. In an example, the step of monitoring properties includes measuring tensile strength of the sample of the proppant and determining a cure time when the tensile strength approaches an asymptotic value. The proppant can be a resin coated curable proppant. The properties monitored can include acoustic velocity of the sample of the proppant, and the method can include determining a cure time when the acoustic velocity approaches an asymptotic value. The method can optionally include transporting the testing device to a second wellsite and repeating the analysis for proppant at the second wellsite. In an example, the proppant sample testing device includes a gas to liquid pressure intensifier, a ram member selectively moveable by the intensifier, an oedometer, and monitor coupled with the oedometer. In this example, the ram member exerts an axial force of at least about 25,000 pounds to the sample of the proppant. One advantage of a testing system with a ram member that exerts an axial force of around 25,000 pounds force is that the overall weight of the system can be at a level suitable for transportation in a vehicle. In one known example of a testing device, the axial force of the ram member is at around 300,000 pounds force, which requires a significantly larger and heavier support structure over that of embodiments disclosed herein. Optionally, a gas in the gas to liquid pressure intensifier can be pressurized to about 2000 pounds per square inch.

Also disclosed herein is a proppant testing device that in one example includes a frame selectively moveable from within a transport vehicle to a wellsite, a vessel mounted in the frame having a sample of proppant disposed therein, a gas to liquid pressure intensifier mounted in the frame, and a ram member selectively moveable by the intensifier into the vessel, so that when proppant is in the vessel and the ram member is moved into the vessel on the proppant, the proppant is compressed to simulate a downhole condition. This example of the device includes sensors coupled with the vessel in communication with the proppant. The sensors are one of a temperature sensor, a pressure sensor, or an acoustic sensor. The vessel can be an oedometer. The device can further optionally include frame mounts on the frame that selectively couple with the transport vehicle, so that when the testing device is transported within the vehicle, the device is secured to the vehicle. Electronics may optionally be included that are in communication with the sensors, in one embodiment a processor is also included that is in communication with electronics, so that when the device is in operation, data signals from the sensors can be received and analyzed to determine information about the proppant. In an example, a source of pressurized gas is included that is selectively in communication with the gas to liquid pressure intensifier, and wherein one of the electronics and processor are in communication with a valve for regulating flow from the source of pressurized gas to the gas to liquid pressure intensifier. A press assembly can be included that is made up of a cylinder, a piston in the cylinder, an inlet on the cylinder in communication with an outlet of the gas to liquid pressure intensifier and in communication with a side of the piston, and a shaft having an end coupled with a side of the piston facing away from the side of the piston in communication with the inlet and another end coupled with the ram member. In an example, the gas to liquid intensifier includes a cylinder having an inlet and an outlet, a piston in the cylinder having a side in communication with the inlet and a side facing the outlet, a seal along a periphery of the piston and an inner surface of the cylinder that defines a barrier to flow between the inlet and outlet, so that when flow from a source of pressurized gas flows through the inlet and into the cylinder, the piston is urged towards the outlet and pressurizes fluid in cylinder between the piston and the outlet that in turn compresses the proppant.

BRIEF DESCRIPTION OF THE DRAWINGS

So that the manner in which the above-recited features, aspects and advantages of the invention, as well as others that will become apparent, are attained and can be understood in detail, a more particular description of the invention briefly summarized above may be had by reference to the embodiments thereof that are illustrated in the drawings that form a part of this specification. It is to be noted, however, that the appended drawings illustrate only preferred embodiments of the invention and are, therefore, not to be considered limiting of the invention's scope, for the invention may admit to other equally effective embodiments.

FIGS. 2A and 2B are side schematic views of an example of testing a proppant sample in accordance with the present invention.

FIG. 3 is a side partial sectional view of an example of testing proppant at a well site with the system of FIG. 1 in accordance with the present invention.

FIG. 4 is a perspective view of an example of an oedometer with sample proppant inside in accordance with the present invention.

FIG. 5 is a side sectional view of an example of a concentric shell oedometer with sample proppant inside in accordance with the present invention.

DETAILED DESCRIPTION OF THE EXEMPLARY EMBODIMENTS

Figure 1:
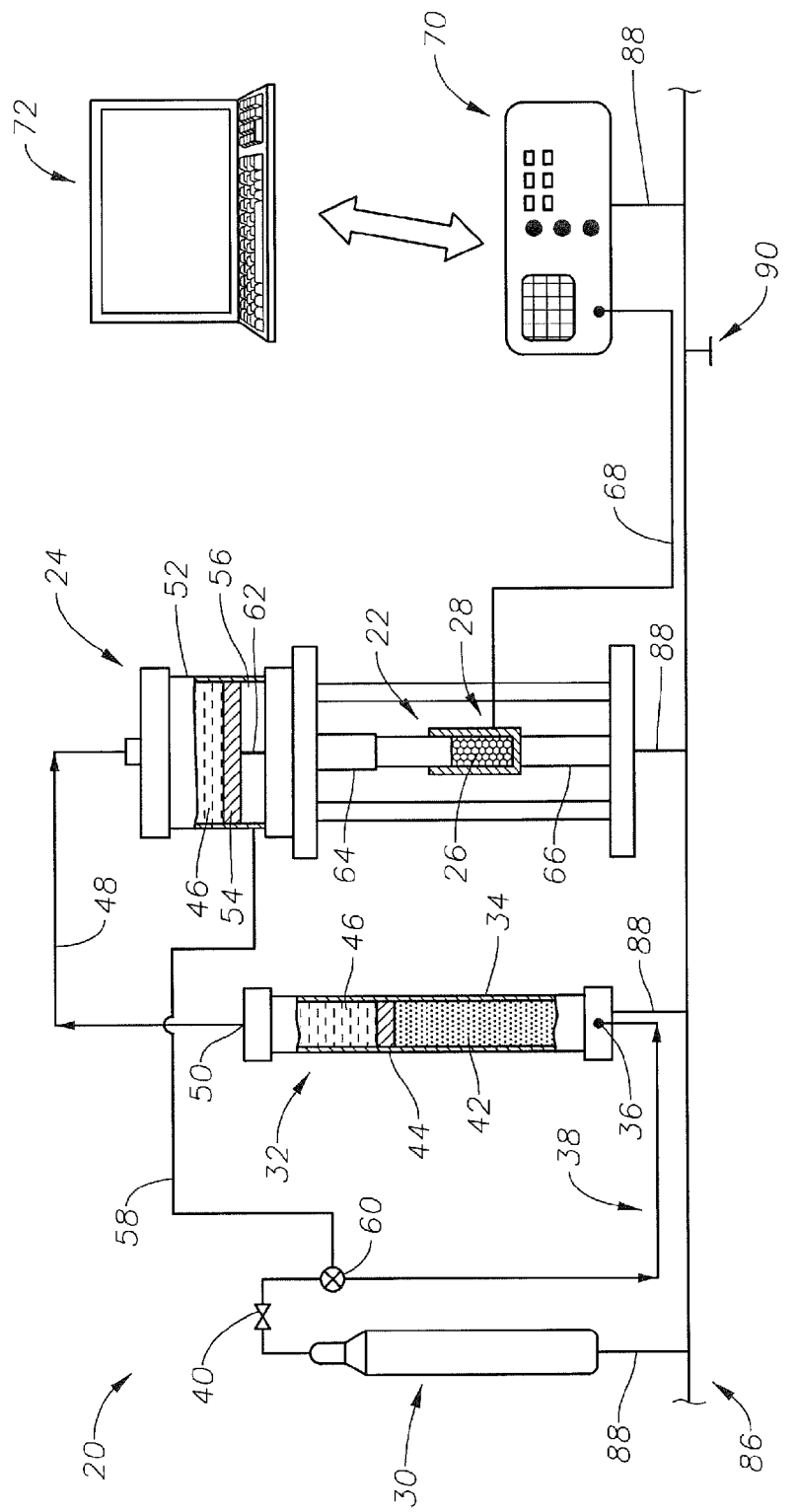
FIG. 1 is a side schematic view of an example embodiment of a portable system for testing proppant in a wellbore in accordance with the present invention.

A testing system 20 for the field testing of resin-coated proppant is schematically illustrated in FIG. 1. The testing system 20 includes a test cell 22 shown mounted within a press assembly 24. The test cell 22 as shown includes a proppant sample 26 disposed in an oedometer 28. As will be described in more detail below, charging the press assembly 24 in turn compresses the proppant sample 26 within the oedometer 28. In an example, the oedometer 28 acts as a vessel for receiving the proppant sample 26. A pressurized fluid supply 30 is schematically illustrated and is used for pressurizing an intensifier 32. The intensifier 32 of FIG. 1 includes an upstream cylinder 34, having a fluid inlet 36 connected to the fluid supply 30 via line 38. A valve 40 is in line 38 for selectively isolating the fluid supply 30 from intensifier 32. Pressurized gas 42 is shown schematically within the upstream cylinder 34 having flowed through line 38 and inlet 36 into the upstream cylinder 34. Also in the upstream cylinder 34 are a piston 44 and hydraulic fluid 46 shown on a side of the piston 44 opposite the gas 42.

In the example of FIG. 1, introducing the pressurized gas 42 into the upstream cylinder 34 exerts a force against piston 44 to urge the piston 44 against the hydraulic fluid 46. The force of the piston 44 against the hydraulic fluid 46 forces fluid 46 from the cylinder 34 and into a line 48 connected to an exit 50 of the upstream cylinder 34. Distal from exit 50, line 48 connects to a downstream cylinder 52, in which is disposed a portion of the fluid 46 having been urged from the upstream cylinder 34. In the example of FIG. 1, diameter of downstream cylinder 52 exceeds diameter of upstream cylinder 34; thus volume per axial length of downstream cylinder 52 exceeds that of upstream cylinder 34. A piston 54 is in the downstream cylinder 52 that has a cross-sectional area greater than cross-sectional area of piston 44. As such, in example embodiments where the hydraulic fluid 46 is a substantially incompressible liquid, piston 54 is urged an axial length within downstream cylinder 54 in response to axial movement of piston 44 in upstream cylinder 34. While piston 54 moves an axial distance less than piston 44, the larger cross sectional area piston 54 exerts an increased output force over that of the smaller area piston 44.

A low pressure side 56 is defined in a space within the downstream cylinder 52 on a side of the piston 54 opposite the hydraulic fluid 46. A line 58 has an end connected to the low pressure side 56 and a distal end connected to valve 60; valve 60 is shown in line 38 and downstream of block valve 40. In the example of FIG. 1, fluid within the low pressure side 56 may be evacuated through line 58 and valve 60 into line 38 thereby producing a closed loop system.

A shaft 62 is schematically illustrated depending from the piston 54 through the low pressure side 56 and into connection with a ram 64 that engages the oedometer 28. Thus, in an example, the compressive force for compacting the proppant sample 26 is delivered from piston 54. The oedometer 28 is shown resting on a mandrel 66 provided in a base portion of the press assembly 24. Signal line 68 may optionally be connected to the oedometer 28 for monitoring conditions within the oedometer 28. Electronics 70 are shown connected to an end of line 68 for interpreting signals monitored by sensors (not shown) on the oedometer 28. A processor 72, which in the example of FIG. 1 is illustrated as a laptop, is shown in communication with electronics 70. Thus, in one example, signals representing various material properties of the proppant 26 may be transmitted via signal line 68 into processor 72 for visual display by an operator. In one example, the electronics, and/or processor 72, are in communication with valve 40 for controlling flow, and/or rate of flow, of gas through line 38.

FIG. 2A provides a schematic example of mechanical testing of a proppant sample 26. More specifically, the sample 26 is set between a pair of platens 74, 76 and a force F is shown applied to platen 74 for compressively failing the proppant sample 26. The force of failure may be recorded and used to assess a property of the sample 26. FIG. 2B illustrates an example of a tensile test wherein a tensile stress of the proppant sample 26 is obtained by applying forces F to lateral sides of a column of the sample 26. In one example, this tensile test is referred to as a Brazilian tensile test.

FIG. 3 provides a side partial sectional view of an example of a test taking place at a wellsite which is adjacent a wellbore 77. Further in the example of FIG. 3, a gravel pack system 78 is illustrated at an opening of the wellbore and used for delivering proppant 79 into fractures 80 shown extending from a wall of the wellbore 77 and into a surrounding formation 81. Further, a packer 82 is set in the wellbore 77 and at a depth above the fractures 80.

A surface truck 84 is illustrated adjacent the wellbore 77 and at surface 85. A transportable version of a testing system 20 (shown in dashed outline) is schematically illustrated set within the truck 84. Referring back to the example of FIG. 1, an optional frame 86 is schematically illustrated included with the system 20 and that is for mounting the components of the system 20 into a modular unit. Further in the example of FIG. 1, the fluid supply 30, intensifier 32, press assembly 24, and electronics 70 are coupled to the frame 86 by connectors 88. A frame mount 90 is included for securing the system 20 within the truck 84. Referring back to the example of FIG. 3, the system 20 can be transported in the truck 84 to a wellsite adjacent to the wellbore 77. In this example, samples of the actual proppant 79 being injected in the fractures 80 can be being tested in the truck 84 while at the wellsite. More specifically, a proppant sample 26, identical to the proppant 79 within wellbore 77, can be set within oedometer 28 (FIG. 1) and conditions of the wellbore 77 simulated within the oedometer 28. As temperatures in a wellbore are often elevated over that of ambient, a heater (not shown) may be provided in conjunction with the oedometer 28. As discussed above, the press assembly 24 (FIG. 1) provides the compressive forces onto the sample 26 that simulate in situ conditions in the wellbore 77. One example of a proppant sample testing method is provided in U.S. Pat. No. 7,712,525, which is assigned to the assignee of the present application, and incorporated herein in its entirety for all purposes. Optionally, the system 20 in the frame 86 can be removed from the truck 84 and to directly adjacent the well for testing of the proppant 79. Further, embodiments exist wherein the truck 84 is a four wheeled vehicle and the like having a cargo area for the system 20, such as for example a carrier van. As such, the system 20 can be transported in or on vehicles that are typically used for passengers without the need for vehicles used primarily for transporting goods, heavy machinery, and the like, i.e. a tractor trailer.

In one example method, during testing, material properties of the proppant sample 26 are monitored; when the properties reach a designated level it may be determined that the proppant sample 26 is properly cured so as to make up a suitable consistency for use in a producing wellbore. Based on a measured amount of time for the proppant sample 26 to attain designated material property(ies), the time of which to leave the well in a shut-in condition may be estimated. In an example, the measured amount of time can simulate a time period from when the proppant 79 flows into the wellbore 77 and to when the proppant 79 cures, when the proppant 79 flows into the fractures 80 and to when the proppant 79 cures, or when the wellbore 77 is shut in and to when the proppant 79 cures. Knowing when the proppant 79 cures under conditions in the wellbore 77 allows well operators to allow the proppant 79 in the fractures 80 to properly cure before removing the packer 82. In one example of testing material properties, it has been discovered that curable resin-coated proppant has a tensile strength that is a function of curing time under a given stress and temperature. A function between tensile strength and curing time was introduced and found that tensile strength approaches an asymptotic value after some time for a given proppant type, curing fluid, stress, and temperature. Thus, a time at which the tensile strength reaches the asymptotic value can be determined to be the shut-in time required to obtain a maximum tensile strength for a given curable resin-coated proppant.

FIG. 4 provides an optional embodiment of an oedometer 28A that is shown having a housing 90 with a substantially circular outer lateral surface, a cavity extending axially from an open end of the housing 90, and terminating adjacent a closed end that is distal from the open end. In the example of FIG. 4, the proppant 26 is placed within the cavity of the housing 90 and a cylindrically-shaped piston head 92 is shown hovering above the opening. Urging the piston head 92 into the cavity exerts a compressive force onto the sample 26 for simulating pressure conditions in the wellbore 77 (FIG. 3). Connector rods 94 schematically illustrate how the ram 64 (FIG. 1) may exert a compressive force onto the piston head 92. Transducers 96, 98 are shown on an upper surface of the piston head 92 and set within the closed end of the housing 90. In the example of FIG. 4, the transducers 96 may be acoustic transmitters and/or receivers for delivering an acoustic wave through the proppant sample 26 for determining material properties of the proppant sample 26. Optionally, the transducers 96, 98 may also measure one or both of temperature and pressure. A liner 100 is shown set within the housing 90 and along the outer circumference of the proppant sample 26. The liner 100 may be formed from a polymer, such as polyether-ether-ketone (PEEK) or a similar material with a low acoustic impedance and high strength at 150 degrees centigrade. In one example, the housing 90 may be formed from a metal, such as a stainless steel.

FIG. 5 is a side sectional view of another optional embodiment of an oedometer 28B. In this example, the oedometer 28B is made up of an outer shell 102 which has a cylindrical outer shape and substantially hollowed out on its inside. The outer shell 102 receives an inner shell 104. Both the outer and inner shells 102, 104 each have a substantially cylindrical outer surface with inner cavity and open end. In the example of FIG. 5, the end of the outer shell 102 having its open end is inserted within the open end of the outer shell 102. Low acoustic impedance liners 106, 108 are shown lining respectively the insides of the outer shell and inner shell 102, 104. Similarly, transducers 96, 98 may be provided on opposing outer sides of the inner and outer shells 102, 104.

An advantage of the gas to oil intensifier allows for stress on the test specimen to be maintained at a constant value throughout the compaction phase of the test and to smoothly load the specimen to failure to measure the unconfined compressive strength. Also, the respective sizes of the upstream and downstream cylinders 34, 52 may be sized so that the movement of the ram 64 may be maintained at a desired length. In one example, the pressure in the pressurized fluid supply 30 may be at least about 2000 pounds per square inch, and the axial force exerted by the ram 64 may be at least about 25,000 pounds. Also, the heater supplied with the oedometer 28 may be able to heat the oedometer to about at least 150 degrees centigrade.

The present invention described herein, therefore, is well adapted to carry out the objects and attain the ends and advantages mentioned, as well as others inherent therein. While a presently preferred embodiment of the invention has been given for purposes of disclosure, numerous changes exist in the details of procedures for accomplishing the desired results. These and other similar modifications will readily suggest themselves to those skilled in the art, and are intended to be encompassed within the spirit of the present invention disclosed herein and the scope of the appended claims.

What is claimed is:

1. A method of testing a proppant used in a wellbore comprising:
   (a) providing a proppant sample testing device that comprises a cylinder containing gas and liquid, a piston in the cylinder separating the gas and the liquid, a ram member selectively moveable in response to pressure changes of the liquid in the cylinder, an oedometer, and monitor coupled with the oedometer;

(b) transporting the testing device to a wellsite having a wellbore in which proppant is being disposed; and (c) disposing a sample of the proppant in the proppant sample testing device, subjecting the sample of the proppant to an estimated wellbore environment in the proppant sample testing device;

(d) applying stress to the proppant by pressurizing the gas in the cylinder so that the liquid in the cylinder is at the same pressure as the gas in the cylinder;

(e) maintaining a magnitude of the stress applied to the proppant at a constant value throughout a compaction phase to smoothly load the proppant to failure;

(f) measuring an unconfined compressive strength based on the step of loading the proppant to failure;

(g) monitoring properties of the sample of the proppant over time; and (h) determining a cure time of the proppant based on the step of monitoring the tensile strength of the proppant.

2. The method of claim 1, further comprising shutting in the wellbore after proppant is disposed in the wellbore for a period of time to define a shut in time, wherein the shut in time is substantially the same as the determined cure time.

3. The method of claim 2, further comprising producing from the wellbore after the expiration of the shut in time.

4. The method of claim 1, wherein the step of monitoring properties comprises measuring tensile strength of the sample of the proppant to determine the cure time when the tensile strength approaches an asymptotic value.

5. The method of claim 1, wherein the cylinder and the piston maintain the applied stress at the constant value throughout the compaction phase.

6. The method of claim 1, wherein the step of monitoring properties comprises measuring acoustic velocity of the sample of the proppant to determine the cure time when the acoustic velocity approaches an asymptotic value.

7. The method of claim 1, wherein the wellsite comprises a first wellsite, the method further comprising transporting the testing device to a second wellsite and repeating steps (a)-(c).

8. The method of claim 1, wherein the gas in the cylinder is pressurized to about 2000 pounds per square inch.

9. A proppant testing device comprising:

a frame selectively moveable from within a transport vehicle to a wellsite;

a vessel mounted in the frame having a sample of proppant disposed therein;

a means for transferring pressure of a gas to a liquid that has a gas side and a liquid side;

a ram member having a side in communication with the liquid side that is at substantially the same pressure as the gas side, and that is selectively moveable by the means for transferring pressure of a gas to a liquid into the vessel, so that when the sample of the proppant is in the vessel and the ram member is moved into the vessel and on the sample of the proppant, the sample of the proppant is compressed to simulate a downhole condition;

sensors coupled with the vessel in communication with the proppant that comprise information gathering devices selected from the group consisting of a temperature sensor, a pressure sensor, and an acoustic sensor; and a processor in communication with the sensors, and that selectively regulates an amount of gas to the gas side, maintains an amount of stress applied to the proppant at a constant value throughout a compaction phase to smoothly load the proppant to failure, measures an unconfined compressive strength based on loading the proppant to failure, monitors the tensile strength of the proppant at failure, and determines a cure time based on the monitored tensile strength.

10. The proppant testing device of claim 9, wherein the vessel comprises an oedometer.

11. The proppant testing device of claim 9, further comprising frame mounts on the frame that selectively couple with the transport vehicle, so that when the proppant testing device is transported within the vehicle, the device is secured to the vehicle.

12. The proppant testing device of claim 9, further comprising electronics in communication with the sensors and a processor in communication with the electronics, so that when the proppant testing device is in operation, data signals from the sensors can be received and analyzed to determine information about the proppant.

13. The proppant testing device of claim 12, further comprising a source of pressurized gas in selective communication with the means for transferring pressure of a gas to a liquid, and wherein one of the electronics and the processor are in communication with a valve for regulating flow from the source of pressurized gas to the means for transferring pressure of a gas to a liquid.

14. The proppant testing device of claim 9, further comprising a press assembly comprising a cylinder, a piston in the cylinder, an inlet on the cylinder in communication with an outlet of the means for transferring pressure of a gas to a liquid and in communication with a side of the piston, and a shaft having an end coupled with a side of the piston facing away from the side of the piston in communication with the inlet and another end coupled with the ram member.

15. The proppant testing device of claim 9, wherein the means for transferring pressure of a gas to a liquid comprises a cylinder having an inlet and an outlet, a piston in the cylinder having a gas side in contact with a source of pressurized gas and a liquid side in contact with liquid that contacts another piston that attaches to the ram, a seal along a periphery of the piston and an inner surface of the cylinder that defines a barrier to flow between the inlet and the outlet, so that when flow from a source of pressurized gas flows through the inlet and into the cylinder, the piston is urged towards the outlet and pressurizes fluid in the cylinder between the piston and the outlet that in turn moves the another piston and the ram and compresses the proppant.

* * * * *